US006218597B1

(12) United States Patent
Port et al.

(10) Patent No.: US 6,218,597 B1
(45) Date of Patent: Apr. 17, 2001

(54) TRANSGENIC MODEL AND TREATMENT FOR HEART DISEASE

(75) Inventors: J. David Port, Denver; Michael R. Bristow, Greenwood Village, both of CO (US)

(73) Assignee: University Technology Corporation, Boulder, CO (US)

(*) Notice: Subject to any disclaimer, the term of this patent is extended or adjusted under 35 U.S.C. 154(b) by 0 days.

(21) Appl. No.: 09/053,293

(22) Filed: Apr. 1, 1998

Related U.S. Application Data (60) Provisional application No. 60/041,966, filed on Apr. 3, 1997.

(51) Int. Cl.$^7$ .......................... C12N 15/09; C12N 15/63; C12N 15/00
(52) U.S. Cl. ........................ 800/18; 800/3; 800/9; 800/21; 800/22; 800/25; 435/455; 435/320.1; 424/9.2
(58) Field of Search .................................... 800/14, 18, 3, 800/9, 21, 22, 25; 435/455, 320.1; 424/9.2

(56) References Cited

U.S. PATENT DOCUMENTS

| | | | |
|---|---|---|---|
| 5,252,479 | 10/1993 | Srivastava | 435/235.1 |
| 5,399,346 | 3/1995 | Anderson et al. | 424/93.21 |
| 5,460,831 | 10/1995 | Kossovsky et al. | 424/493 |
| 5,521,291 | 5/1996 | Curiel et al. | 530/391 |
| 5,559,099 | 9/1996 | Wickham et al. | 514/44 |

FOREIGN PATENT DOCUMENTS

| | | |
|---|---|---|
| 94/04668 | 3/1994 | (WO). |
| 96/14876 | 5/1996 | (WO). |

OTHER PUBLICATIONS

Bertin et al., 1993, *Cardiovascular Research*, 27:1606–1612.
Bisognane et al., Abstract for Biomedicine '97, Apr. 25–27, 1997.
Drazner et al., 1997, *J. Clin. Invest.*, 99(2):288–296.
Gaudin et al., 1995, *J. Clin. Invest.*, 95:1676–1683.
Iwase et al., 1996, *Circulation Research*, 78(4):517–524.
Kirshenbaum et al., 1993, *J. Clin. Invest.*, 92:381–387.
Koch et al., 1995, *Science*, 268:1350–1353.
Milano et al., 1994, *Science*, 264:582–586.
Milano et al., 1994, *Proc. Natl. Acad. Sci. USA*, 91:10109–10113.
Milano et al., 1995, *J. Thorac Cardiovasc Surg*, 109:236–241.
Port et al., *JACC*, 177A (abstract 831–6) (Feb. 1998).
Rohrer et al., 1996, *Proc. Natl. Acad. Sci. USA*, 93:7375–7380.
Samama et al., 1997, *Proc. Natl. Acad. Sci. USA*, 94:137–141.
Soloveva et al., *Mol Endo*, 11(1):27–38.
Adolph et al, *J. Biol. Chem.*, 268(8):5349–5352 (1993).
Frielle et al., *Proc. Natl. Acad. Sci. USA*, 84:7920–7924 (1987).
Gulick et al., *J. Biol. Chem.*, 266(4):9180–9185 (1991).
Jaber et al., *Proc. Natl. Acad. Sci. USA*, 93:12974–12979 (1996).
Kenakin, *Pharmacological Reviews*, 48(3):413–463 (1996).
Korzick et al., *Am. J. Physiol.*, 272(*Heart Circ. Physiol.* 41):H590–H596 (1997).
Tate et al., *Eur. J. Biochem.*, 196:357–361 (1991).
Turki et al., *Proc. Natl. Acad. Sci. USA*, 93:10483–10488 (1996).
Yoshikawa et al., *Eur. Heart Journal*, 17(Supp B):8–16 (1996).
Hammer et al., Journal of Animal Science, vol. 63, pp. 269–278, 1986.*
Elbert et al., Molecular Endocrinology, vol. 2, pp. 277–283, 1988.*
Mullins et al., Journal of Clinical Investigations, 98, No. 11, pp. S37–S40, 1996.*
Wall, Theriogenology, vol. 45, pp. 57–68, 1996.*
Kapple et al., Current Opinion in Biotechnology, vol. 3, pp. 548–553, 1992.*
Strojek & Wagner, Genetic Engineering: Principles and Methods, vol. 10, pp. 221–246, 1988.*

* cited by examiner

*Primary Examiner*—Jasmine Chambers
*Assistant Examiner*—Jill D. Martin
(74) *Attorney, Agent, or Firm*—Fulbright & Jaworski, LLP (57) ABSTRACT

The invention provides a transgenic mouse that is a model for heart muscle disease and heart failure. Also provided are methods of using the transgenic mouse model to study heart muscle disease and heart failure and conditions and treatments related thereto.

23 Claims, 3 Drawing Sheets

(2 of 3 Drawing Sheet(s) Filed in Color)

TRANSGENIC MODEL AND TREATMENT FOR HEART DISEASE

This application claims benefit of provisional application 60/041,966 filed Apr. 3, 1997.

FIELD OF THE INVENTION

The present invention relates to a transgenic model of heart muscle disease (cardiomyopathy) and heart failure. The present invention also relates to gene therapy for the treatment of heart failure.

BACKGROUND OF THE INVENTION

Heart failure is a pathophysiological condition in which the heart fails to pump blood at a rate commensurate with the requirements of the metabolizing tissues of the body. Heart failure is a principal complication of virtually all forms of heart disease.

In the failing human heart, numerous changes occur in receptor signal transduction pathways. In particular, there is impairment of the myocardial β-adrenergic receptor (βAR) system.

Receptors coupled to heterotrimeric guanine nucleotide-binding proteins (G proteins), such as the adrenergic receptors, increase cellular concentrations of second messengers, such as cyclic adenosine 3', 5'-monophosphate (cAMP), thereby regulating cellular function. The binding of the catecholamines norepinephrine and epinephrine to βARs in the heart stimulates adenylyl cyclase, raises the concentration of cAMP, and increases cardiac contractility. Increased secretion of catecholamines and stimulation of myocardial βARs are critical for augmenting cardiac function during exercise and stress.

One of the best documented changes that occurs in heart failure is the differential down-regulation of the $\beta_1$-adrenergic receptor ($\beta_1$AR). This is accompanied by an uncoupling of the $\beta_2$-adrenergic receptor ($\beta_2$AR) and, perhaps, also the $\beta_1$AR, from adenylyl cyclase stimulation so that the failing heart is less able to respond to βAR agonists and to the demands of stress and exercise. In addition, the $\beta_1$AR signal transduction pathway is presumed to be responsible for producing adverse biological effects in cardiac myocytes associated with chronic activation of the adrenergic nervous system. Therefore, chronic overstimulation of this receptor pathway may contribute significantly to the downward progression of heart failure.

Bertin et al. have described a transgenic mouse overexpressing human $\beta_1$AR. Bertin et al., *Cardiovasc. Res.*, 27, 1606–1612 (1993); PCT application WO 94/04668. Receptor overexpression was targeted exclusively to the atria by using the human a trial natriuretic factor promoter. Statistically significant phenotypic effects were not generated, although an excess of premature supraventricular beats was observed in 43% of the transgenic mice.

Milano et al. have described the creation of a transgenic mouse overexpressing the human $\beta_2$AR using a murine α-myosin heavy chain (αMHC) promoter. Milano et al., *Science*, 264, 582–586 (1994); Milano et al., *J. Thoracic Cardiovasc. Surg.*, 109, 236–241 (1995). The use of this promoter targeted gene expression to the myocardium, both in the atria and ventricles. Myocardial and ventricular function were reported to be enhanced. No pathologic changes were observed in mice up to four months of age. In particular, no heart failure or cardiomyopathic phenotype was reported.

Milano et al. suggest the potential of their approach for the treatment of heart failure by gene therapy. However, they teach against using genes coding for $\beta_1$ARs (see page 583, second column of Milano et al., *Science*, 264, 582–586 (1994)).

SUMMARY OF THE INVENTION

The invention provides a transgenic mouse having incorporated into its genome a transgene comprising a heart tissue-specific promoter operatively linked to a coding sequence comprising DNA coding for a $\beta_1$-adrenergic receptor, the transgene being expressed in at least the myocardium of the heart of the transgenic mouse. The transgenic mouse of the invention can be used a model of heart muscle disease (cardiomyopathy) and may be used to study molecular and cellular aspects associated with heart muscle disease, to identify compounds useful for treating or preventing heart muscle disease, and to evaluate the effects of external factors (such as diet and exercise) on heart muscle disease. As the transgenic mouse of the invention ages, it developes into a model of heart failure and may be used to study molecular and cellular aspects associated with heart failure, to identify compounds useful for treating or preventing heart failure, and to evaluate the effects of external factors (such as diet and exercise) on heart failure. The transgenic mouse of the invention may also be used to study the effects associated with overexpression of $\beta_1$-adrenergic receptors and to evaluate the effects of compounds which interact with $\beta_1$-adrenergic receptors.

The invention further provides a transgenic mammal having incorporated into its genome a transgene comprising a heart tissue-specific promoter operatively linked to a coding sequence comprising DNA coding for a $\beta_1$-adrenergic receptor, the transgene being expressed in at least the myocardium of the heart of the transgenic mammal. This transgenic mammal is also a model of heart muscle disease and heart failure.

Finally, the invention provides a method of treating heart failure in a mammal. The method comprises administering a transgene to the mammal, the transgene comprising a heart tissue-specific promoter operatively linked to a coding sequence comprising DNA coding for a $\beta_1$-adrenergic receptor, the transgene being expressed in at least the myocardium of the heart of the mammal.

BRIEF DESCRIPTION OF THE DRAWINGS

This application contains at least one drawing executed in color.

DETAILED DESCRIPTION OF THE PRESENTLY PREFERRED EMBODIMENTS OF THE INVENTION

The invention provides a transgenic mammal having incorporated into its genome a transgene comprising a heart tissue-specific promoter operatively linked to a coding sequence comprising DNA coding for a $\beta_1$-adrenergic receptor ($\beta_1$AR), the transgene being expressed in at least the myocardium of the heart of the transgenic mammal. In particular, the invention provides a transgenic mammal overexpressing $\beta_1$AR in heart tissue, particularly myocardial tissue. As used herein "overexpress" means a level of $\beta_1$AR expression (total expression including endogenous expression and expression from the transgene) which exceeds the level of $\beta_1$AR expression (endogenous expression only) by transgene-negative animals. Preferably, the level of $\beta_1$AR expression of the transgenic animal is at least 2-fold the level of $\beta_1$AR expression by transgene-negative animals, more preferably at least 20-fold the level of $\beta_1$AR expression by transgene-negative animals, even more preferably at least 30-fold the level of $\beta_1$AR expression by transgene-negative animals, most preferably at least 40-fold the level of $\beta_1$AR expression by transgene-negative animals.

As described in the Examples, transgenic mice overexpressing $\beta_1$AR in heart myocardial tissue display the following phenotype. Histopathological examination demonstrated substantial myocardial remodeling (including cardiomyocyte hypertrophy, interstitial replacement fibrosis, myofibrilar disarray and abnormal nuclear morphology) in all trangenic mice, regardless of age. Echocardiography did not demonstrate any change in heart function in young transgenic mice. Old transgenic mice exhibited greater left ventricular interior chamber dimension in both systole and diastole and reduction in percent fractional shortening compared to young and old control mice and to young transgenic mice. Some of the old transgenic mice had significantly decreased ejection fractions compared to other groups. Thus, young transgenic mice are a useful model of heart muscle disease. As the transgenic mice age, some of them develop into a model of heart failure. As is apparent, the transgenic mice will be particularly valuable as models for studying the development of heart muscle disease and heart failure, particularly the progression from heart muscle disease to heart failure. As used herein, "young" mice are those of about 4–7 months of age (mice younger than 4 months of age have not been evaluated), and "old" mice are those of about 8 months of age or older.

According to the present invention, any non-human animal suitable for the study of heart disease and heart failure may be used as a starting organism for the preparation of a transgenic animal of the present invention. Preferably, the transgenic model of the present invention is a mammal including, but not limited to, pigs, rabbits, primates and rodents. Most preferably, a transgenic model of the present invention is a rodent, and even more preferably, a mouse.

The preparation and uses of the transgenic animal model of the invention will be described below with particular reference to a transgenic mouse. However, the transgene and methods and uses for the transgenic mouse of the present invention, as described below in detail, can be modified and applied to any suitable mammal for the study of heart muscle disease.

According to the present invention, a transgenic mouse is a mouse which includes a recombinant nucleic acid molecule (i.e., transgene) that has been introduced into the genome of the mouse at the embryonic stage of the mouse's development. As such, the transgene will be present in all of the germ cells and somatic cells of the mouse. Methods for the introduction of a transgene into a mouse embryo are known in the art and are described in detail in Hogan et al., *Manipulating the Mouse Enbryo. A Laboratory Manual*, Cold Spring Harbor press, Cold Spring Harbor, N.Y., 1986, which is incorporated herein by reference in its entirety. See also U.S. Pat. Nos. 4,736,866, 5,387,742, 5,545,806, 5,487, 992, 5,489,742, 5,530,177, 5,523,226, 5,489,743, 5,434,340, and 5,530,179. For example, a recombinant nucleic acid molecule (i.e., transgene) can be injected into the pronucleus of a fertilized mouse egg to cause one or more copies of the recombinant nucleic acid molecule to be retained in the cells of the developing mouse. A mouse retaining the transgene, also called a "founder" mouse, usually transmits the transgene through the germ line to the next generation of mice, establishing transgenic lines. According to the present invention, a transgenic mouse also includes all progeny of a transgenic mouse that inherit the transgene.

According to the present invention, a transgene-negative littermate is a mouse which is born into the same litter as a transgenic mouse described herein (i.e., a littermate), but does not inherit the transgene (i.e., is transgene-negative). Such a mouse is essentially a normal, or wild-type, mouse and is useful as an age-matched control for the methods described herein.

The $\beta_1$AR transgene is constructed and cloned by standard methods known in the art. Such standard methods are disclosed, for example, in Sambrook et al., 1989, *Molecular Cloning: A Laboratory Manual*, Cold Spring Harbor Labs Press. The reference Sambrook et al., ibid., is incorporated herein by reference in its entirety.

In the transgenic mouse described herein, the transgene includes DNA coding for a $\beta_1$AR. Preferably the DNA codes for human $\beta_1$AR. $\beta_1$AR clones are known. See, e.g., Tate et al., *Eur. J. Biochem.*, 196, 357–361 (1991); Yoshikawa et al., *Eur. Heart J.*, 17 (Supp. B) 8–16 (1996); Kenakin, *Pharmacol. Rev*, 48, 413 (1996). Other clones can be isolated using standard methods known in the art. Alternatively, DNA coding for a $\beta_1$AR can be synthesized by chemical synthetic methods known in the art using known sequences. The transgene may contain a single copy or multiple copies of the $\beta_1$AR coding sequence (increasing the copy number of the $\beta_1$AR coding sequence will increase expression of $\beta_1$AR)

In addition to the DNA coding for $\beta_1$AR, the transgene is constructed to include a promoter selected to drive expression of the $\beta_1$AR exclusively in the heart and in at least the myocardium, preferably predominantly in the myocardium. Preferably, the promoter is an $\alpha$-myosin heavy chain ($\alpha$MHC) promoter.

In addition to the promoter, the transgene will contain other expression control sequences necessary or desirable for proper expression and processing of the $\beta_1$AR. These expression control sequences and the promoter will be operatively linked to the $\beta_1$AR-encoding DNA. The phrase "operatively linked" refers to linking of nucleic acid sequences in the transgene in a manner such that the $\beta_1$AR can be expressed in cardiac cells when the transgene is integrated into a host genome. The additional expression control sequences are well known in the art and include sequences which control the initiation, elongation, and termination of transcription (such as enhancer sequences and polyadenylation sequences).

Transgene sequences are cloned using a standard cloning system, and the transgene products are excised from the cloning vector, purified, and injected into the pronuclei of fertilized mouse eggs. Stable integration of the transgene into the genome of the transgenic embryos allows permanent transgenic mouse lines to be established.

Mouse strains which are suitable for the derivation of transgenic mice as described herein are any common laboratory mouse strain. Preferred mouse strains to use for the derivation of transgenic mice founders of the present invention include FVB and C57 strains. Preferably, founder mice are bred onto wild-type mice to create lines of transgenic mice.

The preparation of transgenic mice overexpressing human $\beta_1$AR in heart myocardial tissue is described in the Examples. Some of these mice were sacrificed, and their heart tissue was examined. A very high abundance of human $\beta_1$AR mRNA was detected in their cardiac tissue. Also, from about a 2-fold to about a 46-fold increase in $\beta_1$AR density, as compared to wild-type mice, was found. The phenotype of the mice was described above.

Another aspect of the present invention is a method of using the transgenic mammals of the invention to study heart muscle disease and heart failure. The characteristics of heart muscle disease and heart failure are well known. See, e.g., *Heart Disease: A Textbook of Cardiovascular Medicine* (5th ed., Braunwald ed., 1997).

In particular, the transgenic mammals of the invention may be used to study the molecular and cellular aspects of heart muscle disease and heart failure. For instance, a transgenic mouse of the present invention may be sacrificed, and the cells and/or tissues examined at the cellular or molecular level and compared to the cells and/or tissues from transgene-negative littermates. Examples of experiments that can be performed include, but are not limited to, morphological examination of cardiac cells; histological examination of coronary vessels, of heart sections, of myocytes and/or of myofibrils; evaluation of cardiac myocyte DNA replication and/or expression; assays to evaluate enzyme activity; and assays of βAR expression and of signal transduction. The methods of performing such experiments are standard and well known in the art.

In addition, the transgenic animals of the invention can be used to study the effects of overexpression of $\beta_1$AR. For instance, the effects of overexpression of $\beta_1$AR on heart morphology and function, myocyte morphology and function, the expression of other molecules, the development and treatment of heart muscle disease and heart failure, can be evaluated. The methods of performing such experiments are standard and well known in the art.

Another embodiment of the present invention relates to a system in which to test drugs candidates for prevention or treatment of heart muscle disease and heart failure. In this embodiment, a transgenic mouse of the invention serves as an in vivo system to evaluate the effect of drug candidates for prevention or treatment of heart muscle disease and heart failure. Specifically, a transgenic mouse of the present invention is administered a candidate drug. The mouse is then evaluated for physiological and pathological changes which indicate the efficacy of the drug for prevention, treatment, or reduction of the rate of progression, of heart muscle disease and/or heart failure. Of particular interest are drugs which prevent heart muscle disease from developing into heart failure, such as β-adrenergic receptor antagonists (β-blockers). A drug refers to any chemical compound that can be administered to an animal as an aid in the diagnosis, treatment or prevention of disease or an abnormal condition.

In addition, the transgenic mice of the invention may be used to evaluate the effects of drugs which interact with or affect $\beta_1$ARs. The effects studied can include effects on the $\beta_1$ARs themselves, effects on heart morphology and function, effects on myocyte morphology and function, effects on signal transduction, effects on the expression of other molecules, and effects on the development and treatment of heart disease and heart failure. For instance, $\beta_1$AR antagonists (i.e., compounds that block, at least partially, an effect of an endogenous adrenergic receptor agonist, such as epinephrine and norepinephrine) can be evaluated as described in provisional application 60/043,906 entitled "Method For Identifying Adrenergic Receptor Antagonists Having Good Tolerability," filed on Apr. 3, 1997, the complete disclosure of which is incorporated herein by reference. Briefly, the inverse agonist activity and intrinsic sympathomimetic activity of a $\beta_1$AR antagonist are measured by methods known in the art. See, e.g., Bond et al., *Nature*, 374, 272–276 (1995); Sponer et al., *J. Cardiovascular Pharmacol.*, 9, 317–327 (1987). See also Kenakin, *Pharmacol. Rev.*, 48, 413 (1996); Samama et al., *Molec. Pharmacol.*, 45, 390–94 (1994); Chidiac et al., *Molec. Pharmacol.*, 45, 490–99 (1994); Samama et al., *J. Biol. Chem.*, 268, 4625–36 (1993); Jasper and Insel, *Biochem. Pharmacol.*, 43, 119–130 (1992); Tate et al., *Eur. J. Biochem.*, 196, 357–361 (1991); *Methods In Enzymology*, volume 200, "Protein Phosphorylation, Part A" (Hunter and Lefton eds.,1991); Port et al., *Circulation*, 81, 929–938 (1990). Compounds having less than about 50% inverse agonist activity (i.e., produces no more than about a 50% reduction in basal adrenergic receptor activity) and less than about 30% intrinsic sympathomimetic activity (i.e., produces no more than about a 30% increase in basal adrenergic receptor activity) are identified. Such compounds have been found to exhibit good tolerability (i.e., exhibit limited adverse side effects in a patient to whom they are administered).

In accordance with the present invention, acceptable protocols to administer a candidate drug include the mode of administration and the effective amount of candidate drug administered to an animal, including individual dose size, number of doses and frequency of dose administration. Determination of such protocols can be accomplished by those skilled in the art, and the determination of such protocols is, in fact, another use of the transgenic mice of the invention. Suitable modes of administration can include, but are not limited to, oral, nasal, topical, transdermal, rectal, and parenteral routes. Preferred parenteral routes can include, but are not limited to, subcutaneous, intradermal, intravenous, intramuscular and intraperitoneal routes. Preferred topical routes include inhalation by aerosol (i.e., spraying) or topical surface administration to the skin of an animal. Preferred is oral administration.

According to the method of the present invention, an effective amount of a candidate drug to administer to an animal comprises an amount that is capable of preventing or treating heart muscle disease or heart failure, or interacting with or affecting $\beta_1$ARs, without being toxic to the animal. An amount that is toxic to an animal comprises any amount that causes damage to the structure or function of an animal (i.e., poisonous). Prevention or treatment of heart muscle disease or heart failure can be assessed as a change (i.e., increase or reduction) in a phenotypic characteristic associated with heart muscle disease or heart failure, such change being indicative of prevention or treatment of heart muscle disease or heart failure.

Yet another embodiment of the present invention relates to the use of a transgenic mouse of the invention to study the effects of external factors on heart muscle disease and heart failure. Such factors include, but are not limited to, diet and exercise. In this embodiment, a transgenic mouse is fed a particular diet or submitted to a particular exercise regimen which is to be studied for its effect on heart muscle disease or heart failure. Such mouse is then monitored for a change in one or more characteristics of heart muscle disease or heart failure in comparison to transgene-negative littermates. For example, the effects of a low-fat diet or of moderate exercise on the development of characteristics associated with heart muscle disease and heart failure can be evaluated using the transgenic mouse model of the present invention.

Yet another embodiment of the present invention relates to a method to study heart muscle disease, heart failure, or overexpression of $\beta_1AR$ by breeding a transgenic mouse of the present invention with other genetically altered mice. Examples of other genetically altered mice which would be candidates for such breeding experiments include mice with manipulations in systems such as the renin-angiotensin system, calcium handling systems, cell signal transduction systems, and adrenergic nervous system. See Milano et al., *Science*, 264, 582–586 (1994); Gaudin et al., *J. Clin. Invest.*, 95, 1676–1683 (1995); Iwase et al., *Circ. Res.*, 78, 517–524 (1996); Bertin et al., *Cardiovasc. Res.*, 27, 1606–1612 (1993); Koch et al., *Science*, 268, 1350–53 (1995); Samama et al., *Proc. Natl. Acad. Sci. USA*, 94, 137–141 (1997); Milano et al., *Proc. Natl. Acad. Sci. USA*, 91, 10109–10113 (1994).

Another embodiment of the present invention is the treatment of heart failure by gene therapy. It is expected that failing hearts will benefit from increased expression of $\beta_1AR$.

The gene therapy method of the invention comprises delivering a transgene coding for $\beta_1AR$ to a patient (a mammal, preferably a human), so that the $\beta_1AR$ is expressed in at least the myocardium of the heart of the recipient. The preparation of transgenes is described above.

The need for gene therapy in a patient can be identified by a variety of methods well known in the art. In particular, patients in need of gene therapy are those who exhibit the normal signs and symptoms of heart failure, especially end-stage heart failure (e.g., New York Heart Association Class IV heart failure). See, e.g., *Heart Disease: A Textbook of Cardiovascular Medicine* (5th ed., Braunwald ed., 1997)

Methods and materials for gene therapy are well known in the art. See Culver, *Gene Therapy: A Primer for Physicians* (Revised 2nd ed., 1996), U.S. Pat. Nos. 5,521,291, 5,460,831 and 5,559,099, PCT application WO 96/14876, all of which are incorporated herein by reference in their entirety. See also, Kirshenbaum, et al., *J. Clin. Invest.*, 92, 381–387 (1993) and Drazner et al., *J. Clin. Invest.*, 99, 288–296 (1997). In particular, suitable methods and vehicles for delivery of transgenes are known and may be used to deliver the $\beta_1AR$ transgene. For instance, naked DNA can be injected directly into the myocardium. Also, targeted vehicles may be used for delivery of the transgene to myocytes. A targeted vehicle is one which includes a component that allows the vehicle to bind to, and deliver the transgene to, a specific cell or tissue. Such targeted vehicles are known in the art. The transgene may be included in a viral vector for delivery to myocytes. Such viral vectors are known in the art. Preferably, the transgene is incorporated into an adenoviral vector for delivery. See Kitsis et al., *Proc. Natl. Acad. Sci. USA*, 88, 4138–4142 (1991); Kass-Eisler et al., *Proc. Natl. Acad. Sci. USA*, 90, 11498–11502 (1993); Akhter et al., *Proc. Natl. Acad. Sci. USA*, 94, 12100–12105 (1997). The transgene is preferably infused directly into the heart by injecting it into the coronary artery, thereby ensuring the greatest amount of transgene absorption into myocytes. The transgene preferably integrates into the host cell's genome to provide for stable transformation.

It is to be noted that the term "a" or "an" entity refers to one or more of that entity. For example, "a characteristic" refers to one or more characteristics or at least one characteristic. As such, the terms "a" (or "an"), "one or more" and "at least one" can be used interchangeably herein. It is also to be noted that the terms "comprising", "including", and "having" can be used interchangeably.

EXAMPLES

Example 1
Production of Transgenic Mice
A. Preparation Of Transgene
The transgene was constructed using standard cloning techniques.

The transgene coding region included a human $\beta_1AR$ cDNA. This cDNA was obtained from Dr. Robert Lefkowitz at Duke University. Its isolation and properties are described in Frielle et al., *Proc. Natl. Acad. Sci. USA*, 84, 7920–7924 (1987).

Using appropriate restriction endonulease sites (EcoRI) within the polylinker region, the cDNA encoding the human $\beta_1AR$ was first subcloned into pBluescript II SK (Stratagene) to facilitate subsequent subcloning. The resulting plasmid was designated pBSIISK$\beta_1AR$.

Figure 1:
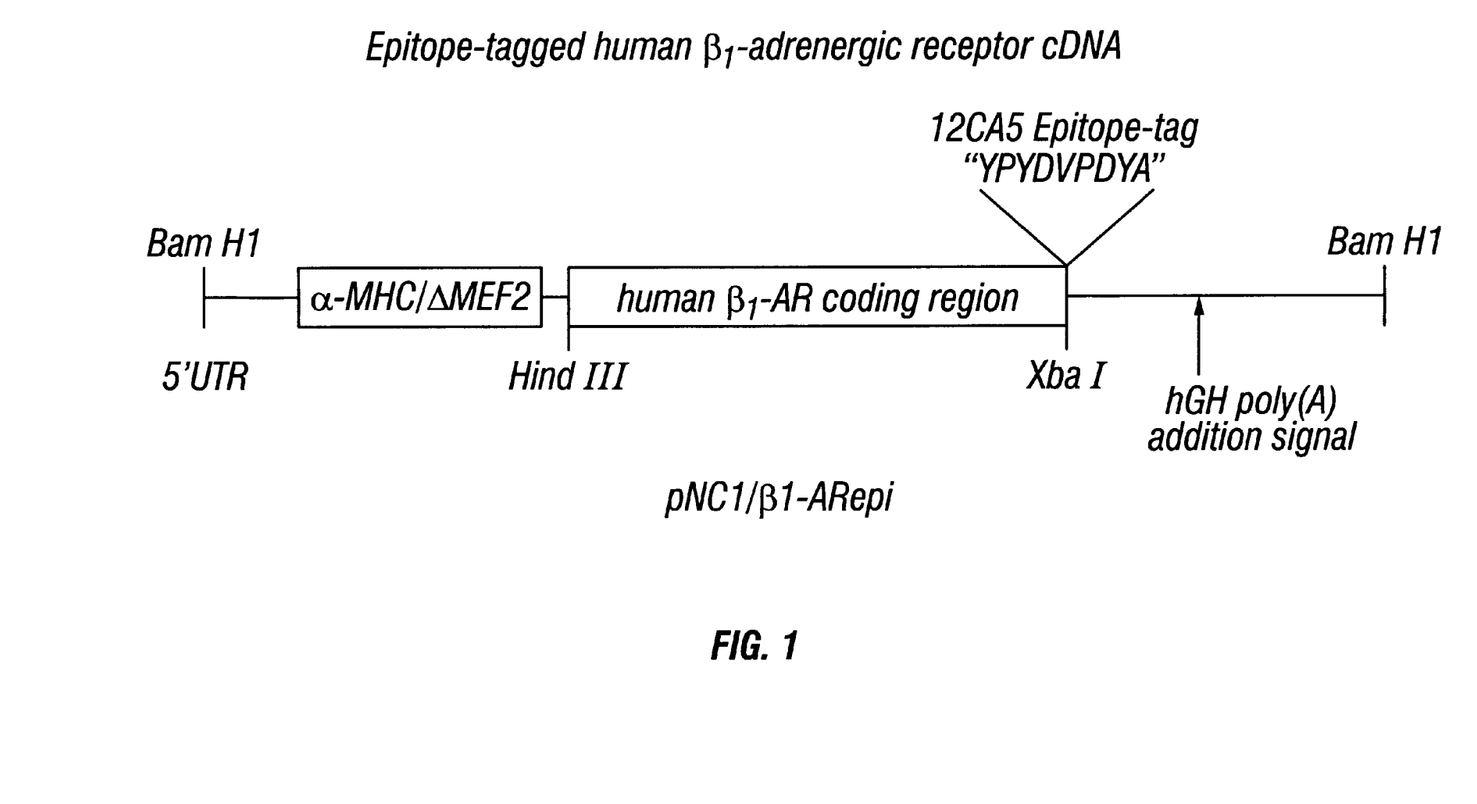
FIG. 1. Diagram of cDNA construct coding for epitope-tagged human $\beta_1$AR in vector pNC1.
Figure 2A:
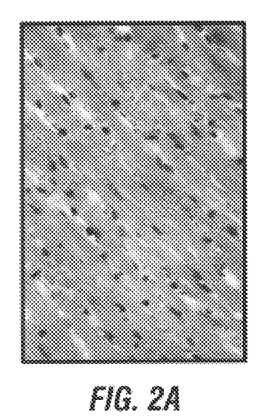
FIGS. 2A–B. Myocardial tissue sections from transgenic mouse (FIG. 2B) and nontransgenic, control mouse (FIG. 2A) stained with hematoxylin and eosin. The transgenic mouse tissue showed marked myocyte hypertrophy with enlarged pleomorphic nuclei.
Figure 2B:
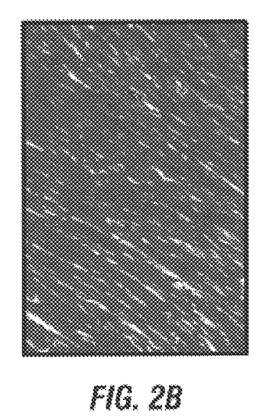
Figure 2C:
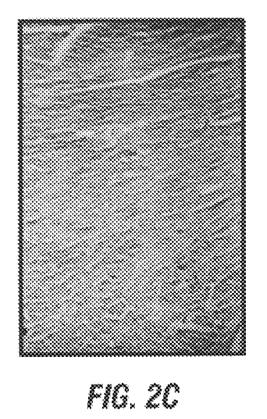
FIGS. 2C–D. Myocardial tissue sections from transgenic mouse (FIG. 2D) and nontransgenic, control mouse (FIG. 2C) stained with Masson's trichrome. The transgenic mouse tissue shows myofibrillar disarray and significant fibrosis.
Figure 2D:
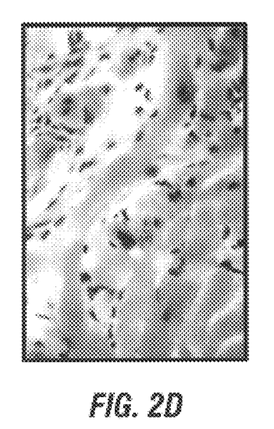
Figure 2E:
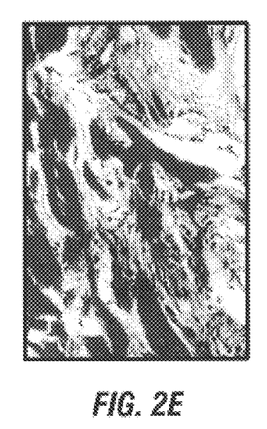
FIGS. 2E–F. Myocardial tissue sections from transgenic mouse (FIG. 2F) and nontransgenic, control mouse littermate (FIG. 2E) stained using HA.11 antibody. Compared to control mouse tissue, significant staining (blue) in the transgenic mouse tissue indicates the presence of human $\beta_1AR_{epi}$ protein.
Figure 2F:
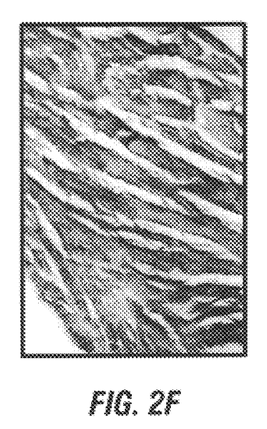

Since an antibody to human $\beta_1AR$ was not available, a nucleotide sequence encoding an epitope tag was added to the DNA coding for $\beta_1AR$. To do so, plasmid pBSIISK$\beta_1AR$ was digested with StyI, which cuts immediately 5' of the stop codon of the $\beta_1AR$ cDNA, and with XbaI, which cuts at a site within the polylinker region. PCR primers were produced such that, when ligated, the nucleotide sequence encoded (5' to 3') a StyI site, the amino acid sequence Tyr Pro Tyr Asp Val Pro Asp Tyr Ala [SEQ ID NO:1], the TAG translational stop codon, and an XbaI site. SEQ ID NO:1 is often referred to as the "12CA5" epitope of hemagglutinin and is recognized by the polyclonal rabbit antibody HA.11 (BabCo, Richmond Calif). The primers were annealed, digested with the appropriate enzymes and ligated into plasmid pBSIISK$\beta_1AR$. PCR was performed using standard methodology as described in *PCR Protocols: A guide to methods and applications* (Innis et al. eds., Academic Press, Inc.,1990). DNA sequencing by the dideoxy method (Sequenace V2, USB) verified that the epitope tag was appropriately subcloned in proper reading frame. A diagram of the cDNA construct coding for epitope-tagged $\beta_1AR$ protein ($\beta_1AR_{epi}$) is presented in FIG. 1.

To appropriately characterize the clone, plasmid pBSIISK$\beta_1AR$ containing the coding sequence for $\beta_1AR_{epi}$ was linearized and in vitro transcribed. Messenger RNA was translated in a rabbit reticulocyte lysate system (RRL, Promega, Inc.) with the inclusion of $^{35}S$-methionine (New England Nuclear). The $\beta_1AR_{epi}$ was immunoprecipitated with the HA.11 antibody. Appropriate expression of $\beta_1AR_{epi}$ protein was verified by immunodetection.

The $\beta_1AR_{epi}$ cDNA was subcloned into the eukaryotic expression vector, pcDNA3 (Invitrogen, Inc.) and expressed stably in CHO-K1 cells (American Type Culture Collection, Rockville, Md.). $\beta_1AR_{epi}$ expression was verified by radio-ligand binding using $^{125}$I-iodocyanopindolol (ICYP), which binds specifically to βAR.

To prepare a DNA construct suitable for producing transgenic mice, the cDNA encoding $\beta_1AR_{epi}$ was subcloned into the HindIII site of the vector, pNC1, obtained from Dr. Jeffrey Robbins at Children's Hospital Research Center, Cincinnati Ohio. This vector is described in Palermo, et al., *Circ. Res.*, 78, 504 (1996). This vector contains a large portion of the α-myosin heavy chain (αMHC) promoter with a point mutation in the MEF-2 binding site. Adolf et al., *J. Biol. Chem.*, 268, 5349–5352 (1993); Gulick et al., *J. Biol. Chem.*, 266, 9180–9185 (1991). A mutation at this site does not affect cardiac localization, but does increase transgene expression. The endogenous $\beta_1AR$ 3' untranslated region (UTR) has been deleted. pNC1 also contains the human growth hormone (hGH) poly(A) addition site downstream from the site of insertion of the coding sequence. The presence and orientation of the $\beta_1AR_{epi}$ cDNA within pNC1 was verified by DNA sequencing and by restriction site mapping. A diagram of the cDNA construct encoding $\beta_1AR_{epi}$ in pNC1 is presented in FIG. 1.

B. Production Of Transgenic Mice

To produce transgenic mice, the vector containing the $\beta_1AR_{epi}$ coding sequence, pNC1/$\beta_1AR_{epi}$, was linearized with BamHI. Following standard protocols (Hogan et al., Manipulating the *Mouse Embryo. A Laboratory Manual*, Cold Spring Harbor press, Cold Spring Harbor, N.Y., 1986), linearized DNA was injected into pronuclei of fertilized FVB/N mouse eggs, and the embryos were transferred into pseudopregnant FVB/N recipient mice (National Institutes Of Health Animal Genetics Resource). These mice have relatively large pronuclei and a high level of reproductive performance.

From six original recipient mice, approximately 28 founder ($F_0$) pups were live-born. Of these, four mice (2 male and 2 female) were confirmed by Southern blotting (see below) to contain the αMHC/$\beta_1AR_{epi}$ transgene. To produce $F_1$ mice, each of the two females was bred to a background FVB/N male and each of the two transgenic males was bred with two background FVB/N females. Approximately 57 $F_1$ mice were live-born. Several $F_1$ mice that were positive by Southern blotting have been mated to FVB/N wild-type mice, and a few $F_2$ mice have been born.

C. Screening Of Transgenic Mice

Transgenic mice were screened in a variety of ways to confirm that they carried the transgene and to characterize the mice.

1. PCR Screening

PCR primers were produced to recognize the 3' region of the αMHC promoter (up-stream primer) and the 5' region of the $\beta_1AR_{epi}$ coding region (down-stream primer) of the transgene. The upstream primers had the following sequences:

5'-CAGGCACCCT TACCCCACAT A-3' [SEQ ID NO:2]

5'-AGAAGCCTAG CCCACACCAG A-3' [SEQ ID NO:3]

The downstream primers had the following sequences:

5'-ACAGCGGCTC GGGGCTTTC-3' [SEQ ID NO:4]

5'-TGCCCGCCAC GATGAGCAGC-3' [SEQ ID NO:5]

Use of these primers gives a unique PCR product of approximately 400 bp. These primers were used to screen mouse genomic DNA as described in Hogan et al., Manipulating the *Mouse Embryo. A Laboratory Manual* (Cold Spring Harbor Press, Cold Spring Harbor, N.Y., 1986).

2. Southern blotting

Southern blots were performed by isolating genomic DNA from mouse tail as described in Hogan et al., Manipulating the *Mouse Embryo. A Laboratory Manual* (Cold Spring Harbor Press, Cold Spring Harbor, N.Y., 1986). Then, 40 μg of genomic DNA were denatured overnight and then digested with EcoRI. The digested DNA was subjected to agarose gel electrophoresis, and the electrophoresed DNA was transferred to a nylon membrane (S&S) and UV cross-linked. UV cross-linking was performed by placing the membranes on ice in a Stratalinker UV source (Stratagene 1800) at 3000 μwatt/cm$^2$ for 5 minutes. The blots were hybridized overnight with an ~1500 bp cDNA fragment of the human $\beta_1AR$ coding region that had been randomly labeled to high specific activity (>×10$^9$ dpm/μg DNA) with $\gamma^{32}$P-dCTP using the "Ready-To-Go" DNA labelling Kit (Pharmacia Biotech). The blot was hybridized overnight in Quickhyb hybridization solution (Stratagene), followed by increasingly stringent washes with SSC (Sambrook et al., 1989, *Molecular Cloning: A Laboratory Manual*, Cold Spring Harbor Labs Press). The blots were visualized by autoradiography.

A band of the expected size (6 Kbp) for the transgene was found in genomic DNA from transgenic mice. A band of this size was not found in genomic DNA from control mice.

3. Ribonuclease Protection Assay (RPA)

To verify appropriate expression of the transgene, $\beta_1AR_{epi}$ mRNA abundance was measured by ribonuclease protection assay (RPA) using an antisense riboprobe as described in Tremmel and Port, *Circulation*, 94, 288–289 (1996) with certain modifications described below. The riboprobe was derived from the coding region of the transgene (nucleotides 150–350) and resulted in 200 nt protected fragments. Radiolabeled ($P^{32}$) riboprobe was generated using the Promega Riboprobe kit (Promega, Madison, Wis., U.S.A.) and purified by guanidinium-acid phenol extraction followed by isopropanol precipitation. Total RNA was isolated from mouse heart using the RNAzol STAT-60 method (Tel-Test Inc., Friendswood, Tex.), a protocol based on quanidinium/isothiocyanate and phenol/chloroform. Five-microgram aliquots of total RNA were analyzed using the RPA II ribonuclease protection kit and protocol (Ambion Inc., Austin Tex.). In each RPA, 10 μg of RNA were hybridized overnight with 5×10$^5$ cpm of radiolabeled $\beta_1AR$ riboprobe (>5-fold molar excess) and 0.6 μg of a low specific activity 18S rRNA riboprobe (Ambion, Inc.). Since 18S rRNA abundance is in excess of mRNA abundance, 18S probe was produced at low specific activity to assure greater than 5-fold molar excess of probe to target without producing a signal beyond the linear range when measured simultaneously with $\beta_1AR$ mRNA. The hybridization reaction with digested with RNase A and RNAse T1. RNA-RNA hybrids were resolved by electrophoresis in an 8% polyacrylamide/8M urea gel. The gels were subjected to autoradiography using Kodak XOMAT AR film. Signal intensities for human $\beta_1AR$ mRNA and the 18S rRNA were determined using an Alpha Innotech IS-1000 Digital Imaging System (San Leandro, Calif.) using the scanning/integration method. Automatic background adjustment appeared unreliable and was not used. The linear range of the mRNA signal for $\beta_1AR$ was determined by comparison of increasing amounts of sense strand RNA (1–1000 μmol) on the autoradiogram.

$\beta_1AR_{epi}$ mRNA was detected in transgenic hearts, but not in control hearts or in transgene-negative-littermate hearts. The same protected fragment was detected in RNA obtained from nonfailing human heart and tsAF8 cells transfected so as to produce human $\beta_1AR$.

4. Membrane Expression of $\beta_1AR$

Sarcolemmal membranes were prepared from transgenic and wild-type FVB/N mice as previously described in Bristow et al., *Circulation*, 84, 1024–1039 (1991). Sarcolemmal membrane expression of $\beta_1AR_{epi}$ was determined using binding of the $\beta AR$-selective radioligand, $^{125}$I-iodocyanopindolol (ICYP), as previously described in Bristow et al., *Circulation*, 84, 1024–1039 (1991).

The average $\beta AR$ density in wild-type FVB/N mice was approximately 40–50 fmol/mg membrane protein. In contrast, cardiac $\beta AR_{epi}$ expression in the first transgenic mouse measured was approximately 2300 fmol/mg membrane protein, an approximately 46-fold increase in $\beta AR$ expression, and $\beta AR_{epi}$ expression in a second transgenic mouse was approximately 1700 fmol/mg membrane protein, an approximately 24-fold increase in $\beta AR$ expression. Cardiac $\beta AR_{epi}$ expression in the $F_1$ transgenic mice produced to date has ranged from approximately 100 fmol/mg membrane protein to approximately 2300 fmol/mg membrane protein, an approximately 2-fold to 46-fold increase in $\beta AR$ expression. The Kd for ICYP has consistently been ~20 pM in both wild-type and transgenic mice.

5. Phenotypic Characteristics

Echocardiography was performed on control and transgenic mice that were either 4–5 months of age (young) or 8–20 months of age (old). To perform the echocardiography, the mice, after sedation with Avertin® (25 mg/100 g body weight in a 50 mg/ml solution), were positioned on a gel "standoff" pad, stomach down, with the extremities restrained in standard fashion. Echocardiography was performed using a Vingmed CFM800 echocardiography machine with a pediatric 7.5 MHz annular array transducer that operates at 9 MHz. Two-dimensional and M-mode images were obtained in the parasternal long and short axis orientations. Spectral Doppler flow patterns were obtained for left ventricular outflow. Two-dimensional and Doppler images were obtained at 48 frames per second with a sampling rate of 200 per second for M-mode and Doppler. The digital data for all images and Doppler were immediately transferred and stored on a Macintosh computer connected to the Vingmed System (Vingmed, Horton, Norway). Echocardiographic measurements of chamber size and wall thickness in systole and diastole were made off-line from the stored data utilizing EchoPac (Vingmed). Left ventricular systolic function was evaluated by fractional shortening (the difference between left ventricular internal diamater in diastole and systole divided by the left ventricular internal diameter in diastole). All measurements were made according to the American Society of Echocardiography Guidelines.

Figure 3A:
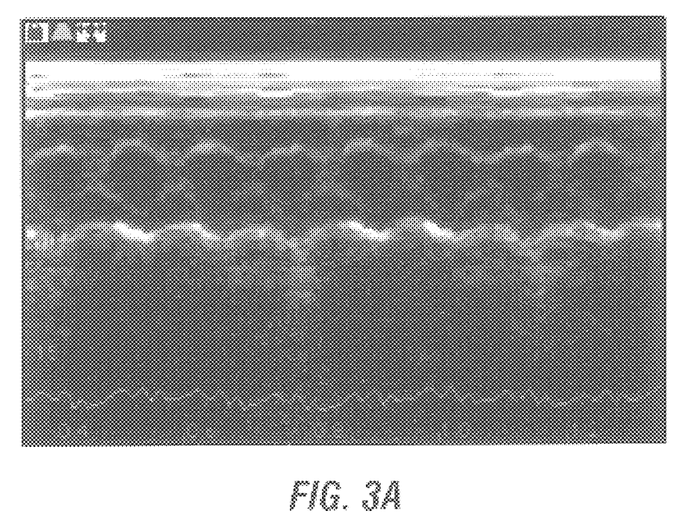
FIGS. 3A–B. Echocardiograms of a control, nontransgenic mouse, approximately 9 months of age (FIG. 3A) and of a $\beta_1$-AR transgenic mouse, approximately 9 months in age (FIG. 3B).
Figure 3B:
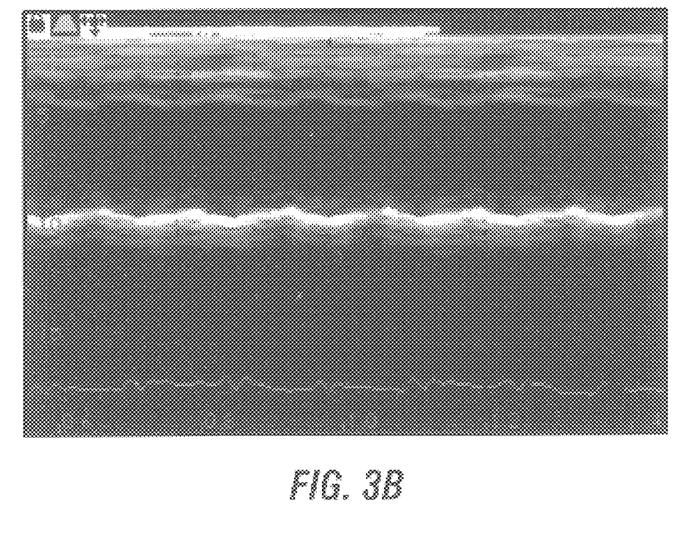

Two echocardiograms (FIGS. 3A–B) demonstrate the dramatic hemodynamic functional differences between an older control (FIG. 3A) and an older transgenic mouse (FIG. 3B). Both mice were about 9 months of age. In the control mouse, close approximation of anterior and posterior ventricular walls in end-systole is readily apparent (fractional shortening (FS) was about 60%). In contrast, in the older transgenic mouse, end-systolic approximation of ventricular walls was very indicative of a substantially reduced fractional shortening (FS was about 30%).

Some of the data from the echocardiographic assessment of cardiac function in several younger and older control and transgenic mice is presented in the table below. As can be seen, old transgenic mice have a tendency towards greater left ventricular interior chamber dimension in both systole (LVIDS) and diastole (LVIDD) and a reduction in percent fractional shortening (FS %) compared to young and old control mice and to young transgenic mice. At an individual animal level, the data were much more compelling. No younger animals (about 4–5 months of age) had any detectable change in FS% or any notable abnormalities in ventricular dimension. In contrast, 2 of 7 old trangenic mice (each about 9 months of age) had ejection fractions of about 30%, representing a decrease of about 50% compared to other groups. These two mice had levels of cardiac $\beta AR$ expression of about 100–150 fmol/mg membrane protein. There was no observed decrease in FS % in older control animals.

|  | CON-yng n = 4 | TG-yng n = 3 | CON-old n = 8 | TG-old n = 7 |
| --- | --- | --- | --- | --- |
| FS (%) | 58 ± 1 | 59 ± 1 | 53 ± 3 | 48 ± 4 |
| LVIDS (mm) | 1.5 ± 0.01 | 1.3 ± 0.05 | 1.6 ± 0.12 | 2.0 ± 0.4 |
| LVIDD (mm) | 3.5 ± 0.04 | 3.2 ± 0.11 | 3.5 ± 0.12 | 3.7 ± 0.2 |

CON = control
TG = transgenic
yng = young

For histopathologic characterization, the hearts of mice were removed, and myocardial tissue sections were formalin fixed, paraffin embedded, cut into $4\mu$ sections. Chamber dilation and wall thickness were evaluated by examining the cut tissue on the slide with the naked eye. Microscopic examination of the tissues was used to evaluate myocardial hypertrophy, myocardial architecture, interstitial fibrosis, and myocardial microvasculature. Some of the tissue sections were stained with hematoxylin and eosin or Masson's trichrome. Also, $\beta_1AR_{epi}$ protein in the sections was detected using HA.11 antibody to the epitope tag (12CA5). Binding of the HA.11 antibody was visualized by incubation with biotinylated secondary antibody, followed by incubation with neutravidin, and then staining with diaminobenzidine (kit from Vector Laboratories, Burlingame Calif., used according to package directions).

There was substantial myocardial remodeling in both old and young transgenic mice, including cardiomyocyte hypertrophy, interstitial replacement fibrosis, myofibrilar disarray, and abnormal nuclear morphology. The results of the staining and immunohistochemistry for a control and a transgenic mouse are shown in FIGS. 2A–F.

Cardiomyocyte apoptosis occurs in animal models of cardiac hypertrophy and failure and in the failing human heart. To determine whether or not expression of certain proteins regulating apoptosis might be altered in damaged regions of the myocardium of the transgenic mice, the distribution of the pro-apoptotic protein, Bax, was examined in formalin-fixed, paraffin embedded mouse hearts using immunohistochemical techniques. Staining of tissue sections with an anti-Bax antibody was performed in hearts from both $\beta_1AR$ transgenic mice and control mice. Bax expression was detected in cardiomyocytes from $\beta_1AR$ transgenic mice, especially near or in regions of fibrosis or in regions in which cardiomyocytes were in disarray. In contrast, Bax expression was very low in the hearts of control, nontransgenic hearts. These data suggest that the abundance of the pro-apoptotic protein, Bax, appears to be highest in fibrotic regions of $\beta_1AR$ transgenic animals. Therefore, Bax expression in cardiomyocytes may be a marker for cellular dysfunction.

The combined results indicate that cardiac overexpression of the $\beta_1AR$ leads to cardiac remodeling and a useful model of heart muscle disease in transgenic mice. Moreover, as the transgenic mice age, they develop into a model of heart failure.

We claim:

1. A transgenic mouse having incorporated into its genome a transgene comprising an α-myosin heavy chain promoter operatively linked to a coding sequence comprising DNA coding for a $\beta_1$-adrenergic receptor, the transgene being expressed in at least the myocardium of the heart of the transgenic mouse such that the transgenic mouse exhibits or develops heart muscle disease.

2. The transgenic mouse of claim 1, wherein the heart tissue of the transgenic mouse exhibits myocardial remodeling.

3. The transgenic mouse of claim 1 or 2, wherein the $\beta_1$-adrenergic receptor is a human $\beta_1$-adrenergic receptor.

4. The transgenic mouse of claim 1 or 2, wherein the coding sequence comprises DNA coding for a fusion protein comprising the $\beta_1$-adrenergic receptor fused to an epitope tag.

5. The transgenic mouse of claim 1 or 2, wherein the level of $\beta_1$-adrenergic receptor expression in the heart of the transgenic mouse is at least about 2-fold greater than the level of $\beta_1$-adrenergic receptor expression in transgene-negative mice.

6. The transgenic mouse of claim 2, wherein the heart tissue of the transgenic mouse exhibits interstitial replacement fibrosis, hypertrophied myocytes, and abnormal nuclear morphology as compared to transgene-negative mice.

7. The transgenic mouse of claim 5, wherein the level of $\beta_1$-adrenergic receptor expression in the heart of the transgenic mouse is at least about 20-fold greater than the level of $\beta_1$-adrenergic receptor expression in transgene-negative mice.

8. The transgenic mouse of claim 7, wherein the level of $\beta_1$-adrenergic receptor expression in the heart of the transgenic mouse is at least about 30-fold greater than the level of $\beta_1$-adrenergic receptor expression in transgene-negative mice.

9. The transgenic mouse of claim 8, wherein the level of $\beta_1$-adrenergic receptor expression in the heart of the transgenic mouse is at least about 40-fold greater than the level of $\beta_1$-adrenergic receptor expression in transgene-negative mice.

10. A method for studying molecular and cellular aspects associated with heart muscle disease comprising the steps of:

(a) harvesting cells, tissues or both from a transgenic mouse having incorporated into its genome a transgene comprising an α-myosin heavy chain promoter operatively linked to a coding sequence comprising DNA coding for a $\beta_1$-adrenergic receptor, the transgene being expressed in at least the myocardium of the heart of the transgenic mouse such that the transgenic mouse exhibits or develops heart muscle disease; and (b) examining the cells, tissue or both from the transgenic mouse to determine if they differ in one or more molecular or cellular aspects from cells and tissues harvested from a transgene-negative mouse in order to identify molecular or cellular aspects associated with heart muscle disease.

11. The method of claim 10 wherein the transgenic mouse exhibits symptoms of heart muscle disease.

12. A method of identifying compounds useful for treating or preventing heart muscle disease comprising the steps of:

providing a first transgenic mouse and a second transgenic mouse, both having incorporated into their genomes a transgene comprising an α-myosin heavy chain promoter operatively linked to a coding sequence comprising DNA coding for a $\beta_1$-adrenergic receptor, the transgene being expressed in at least the myocardia of the hearts of the transgenic mice such that both transgenic mice exhibit or develop heart muscle disease;

administering a compound to be evaluated to the first transgenic mouse; and evaluating physiological and pathological changes in the first transgenic mouse compared to the second transgenic mouse that did not receive the compound to determine the efficacy of the compound in treating or preventing heart muscle disease.

13. The method of claim 12 wherein the transgenic mice exhibit symptoms of heart muscle disease.

14. A method for evaluating the effects of external factors selected from the group consisting of diet and exercise on heart muscle disease comprising the steps of:

(a) establishing a normal control regimen for an external factor selected from the group consisting of diet and exercise in a first transgenic mouse and a second transgenic mouse, both having incorporated into their genomes a transgene comprising an α-myosin heavy chain promoter operatively linked to a coding sequence comprising DNA coding for a $\beta_1$-adrenergic receptor, the transgene being expressed in at least the myocardia of the hearts of the transgenic mice such that both transgenic mice exhibit or develop heart muscle disease;

(b) modulating the regimen for the external factor in the second transgenic mouse; and (c) monitoring the second transgenic mouse for a difference in a characteristic associated with heart muscle disease compared to the first transgenic mouse.

15. The method of claim 14 wherein the transgenic mice exhibit symptoms of heart muscle disease.

16. A method for studying molecular and cellular aspects associated with heart failure comprising the steps of:

(a) harvesting cells, tissues or both from a transgenic mouse having incorporated into its genome a transgene comprising an α-myosin heavy chain promoter operatively linked to a coding sequence comprising DNA coding for a $\beta_1$-adrenergic receptor, the transgene being expressed in at least the myocardium of the heart of the transgenic mouse such that the transgenic mouse exhibits or develops heart muscle failure; and (b) examining the cells, tissue or both from the transgenic mouse to determine if they differ in one or more molecular or cellular aspects from cells and tissues harvested from a transgene-neaative mouse in order to identify molecular or cellular aspects associated with heart failure.

17. The method of claim 16 wherein the transgenic mouse exhibits symptoms of heart failure.

18. A method of identifying compounds useful for treating or preventing heart failure comprising the steps of:

providing a first transgenic mouse and a second transgenic mouse, both having incorporated into their genomes a transgene a transgene comprising an α-myosin heavy chain promoter operatively linked to a coding sequence comprising DNA coding for a $\beta_1$-adrenergic receptor, the transgene being expressed in at least the myocardia of the hearts of the transgenic mice such that both transgenic mice exhibit or develop heart muscle failure;

administering a compound to be evaluated to the first transgenic mouse; and evaluating physiological and pathological changes in the first transgenic mouse compared to the second transgenic mouse that did not receive the compound to determine the efficacy of the compound in treating or preventing heart failure.

19. The method of claim 18 wherein the transgenic mice exhibit symptoms of heart failure.

20. A method for evaluating the effects of external factors selected from the group consisting of diet and exercise on heart failure comprising the steps of:

(a) establishing a normal control regimen for an external factor selected from the group consisting of diet and exercise in a first transgenic mouse and a second transgenic mouse, both having incorporated into their genomes a transgene comprising an α-myosin heavy chain promoter operatively linked to a coding sequence comprising DNA coding for a $\beta_1$-adrenergic receptor, the transgene being expressed in at least the myocardia of the hearts of the transgenic mice such that both transgenic mice exhibit or develop heart failure;

(b) modulating the regimen for the external factor in the second transgenic mouse; and (c) monitoring the second transgenic mouse for a difference in a characteristic associated with heart failure compared to the first transgenic mouse.

21. The method of claim 20 wherein the transgenic mice exhibit symptoms of heart failure.

22. A transgenic mouse having incorporated into its genome a transgene comprising an α-myosin heavy chain promoter operatively linked to a coding sequence comprising DNA coding for a $\beta_1$-adrenergic receptor, the transgene being expressed in at least the myocardium of the heart of the transgenic mouse such that the transgenic mouse exhibits or develops heart failure.

23. The transgenic mouse of claim 22, wherein the mouse exhibits greater left ventricular interior chamber dimension in both systole and diastole and reduced percent fractional shortening as compared to the heart tissue of transgene-negative mice.

* * * * *

UNITED STATES PATENT AND TRADEMARK OFFICE
CERTIFICATE OF CORRECTION

PATENT NO.    : 6,218,597 B1
DATED         : April 17, 2001
INVENTOR(S)   : Port et al.

It is certified that error appears in the above-identified patent and that said Letters Patent is hereby corrected as shown below:

<u>Column 17, claim 16,</u>
Line 4, please delete "transgene-neaative" and insert -- transgene-negative -- therefor.

Signed and Sealed this

Fourth Day of December, 2001

Attest:

*Nicholas P. Godici*

NICHOLAS P. GODICI
*Attesting Officer*    *Acting Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

Tyr Pro Tyr Asp Val Pro Asp Tyr Ala
1               5

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:2:

CAGGCACCCT TACCCCACAT A                                              21

(2) INFORMATION FOR SEQ ID NO:3:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:3:

AGAAGCCTAG CCCACACCAG A                                              21

(2) INFORMATION FOR SEQ ID NO:4:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:4:

ACAGCGGCTC GGGGCTTTC                                                 19

(2) INFORMATION FOR SEQ ID NO:5:

(i) SEQUENCE CHARACTERISTICS:
       (A) LENGTH: 20 base pairs
       (B) TYPE: nucleic acid
       (C) STRANDEDNESS: single
       (D) TOPOLOGY: linear -continued

```
      (ii) MOLECULE TYPE: other nucleic acid
           (A) DESCRIPTION: /desc = "primer"

(xi) SEQUENCE DESCRIPTION: SEQ ID NO:5:

TGCCCGCCAC GATGAGCAGC                                                     20
```